US012625122B2

(12) United States Patent
Knudsen

(10) Patent No.: US 12,625,122 B2
(45) Date of Patent: May 12, 2026

(54) METHOD AND AN UNMANNED AERIAL VEHICLE FOR DETERMINING EMISSIONS

(71) Applicant: EXPLICIT APS, Kgs. Lyngby (DK)

(72) Inventor: Jon Knudsen, Kgs. Lyngby (DK)

(73) Assignee: EXPLICIT APS, Virum (DK)

( * ) Notice: Subject to any disclaimer, the term of this patent is extended or adjusted under 35 U.S.C. 154(b) by 244 days.

(21) Appl. No.: 18/274,648

(22) PCT Filed: Jan. 27, 2022

(86) PCT No.: PCT/EP2022/051867
§ 371 (c)(1),
(2) Date: Jul. 27, 2023

(87) PCT Pub. No.: WO2022/162053
PCT Pub. Date: Aug. 4, 2022

(65) Prior Publication Data
US 2024/0110902 A1 Apr. 4, 2024

(30) Foreign Application Priority Data

Jan. 27, 2021 (EP) ..................................... 21153830

(51) Int. Cl.
*G01N 33/00* (2006.01)
*B64U 10/14* (2023.01)
(Continued)

(52) U.S. Cl.
CPC ..... *G01N 33/0073* (2013.01); *G01N 33/0062* (2013.01); *G05D 1/46* (2024.01);
(Continued)

(58) Field of Classification Search
CPC ........... G01N 33/0073; G01N 33/0062; G01N 21/85; G05D 1/46; G05D 1/646;
(Continued)

(56) References Cited

U.S. PATENT DOCUMENTS 4,135,092 A 1/1979 Milly
2017/0003684 A1* 1/2017 Knudsen ............ G01N 21/3504
(Continued)

FOREIGN PATENT DOCUMENTS

EP 2625500 B1 4/2015
WO 2019210375 A1 11/2019
(Continued)

OTHER PUBLICATIONS

Golston et al., "Natural Gas Fugitive Leak Detection Using an Unmanned Aerial Vehicle: Localization and Quantification of Emission Rate", Atmosphere, Aug. 23, 2018, pp. 1-17.
(Continued)

*Primary Examiner* — Ryan D Walsh
(74) *Attorney, Agent, or Firm* — Workman Nydegger

(57) ABSTRACT

A method is provided for determining emissions from at least one source by inspection at an inspection area. The emissions include the presence or concentration of at least one predetermined gas and/or particles. An unmanned aerial vehicle (UAV) and the collection of wind data is obtained by a moving UAV using at least one wind sensor.

14 Claims, 11 Drawing Sheets

(51) Int. Cl.
  B64U 101/00 (2023.01)
  B64U 101/35 (2023.01)
  G01N 21/85 (2006.01)
  G05D 1/46 (2024.01)
  G05D 1/646 (2024.01)
  G05D 1/689 (2024.01)

(52) U.S. Cl.
  CPC ............. *G05D 1/646* (2024.01); *G05D 1/689*
    (2024.01); *B64U 10/14* (2023.01); *B64U*
    *2101/00* (2023.01); *B64U 2101/35* (2023.01);
    *B64U 2201/10* (2023.01); *G01N 21/85*
    (2013.01)

(58) Field of Classification Search
  CPC .... G05D 1/689; B64U 10/14; B64U 2101/00;
    B64U 2101/35; B64U 2201/10
  See application file for complete search history.

(56) References Cited

U.S. PATENT DOCUMENTS

| | | | |
|---|---|---|---|
| 2018/0127093 A1 | 5/2018 | Christensen et al. | |
| 2020/0033157 A1 | 1/2020 | Kaufman et al. | |
| 2020/0217742 A1 | 7/2020 | Steele et al. | |
| 2020/0355580 A1 | 11/2020 | Asher | |
| 2021/0140934 A1* | 5/2021 | Smith | G05D 1/0022 |
| 2025/0003938 A1* | 1/2025 | Bourlon | G01N 33/0062 |

FOREIGN PATENT DOCUMENTS

| | | |
|---|---|---|
| WO | 2019246280 A1 | 12/2019 |
| WO | 2019246283 A1 | 12/2019 |
| WO | 2020086499 A1 | 4/2020 |

OTHER PUBLICATIONS

Ravikumar et al., "Single-Blind Inter-Comparison of Methane Detection Technologies—Results from the Stanford/ EDF Mobile Monitoring Challenge", Elementa Science of the Anthropocene, vol. 7, Sep. 10, 2019, pp. 1-16.
"Measuring Airflow with a Pitot Tube", Trutechtools, Jan. 15, 2021, pp. 1-3.
Extended European Search Report from corresponding European Patent Application No. EP21153830.1, Jun. 30, 2021.
International Search Report from corresponding PCT Application No. PCT/EP2022/051867, Apr. 26, 2022.
International Preliminary Report on Patentability from corresponding PCT Application No. PCT/EP2022/051867, Feb. 24, 2023.

\* cited by examiner

METHOD AND AN UNMANNED AERIAL VEHICLE FOR DETERMINING EMISSIONS

TECHNICAL FIELD

The present invention relates to a method for determining emissions from at least one source by inspection at an inspection area, said emissions comprising the presence or concentration of at least one predetermined gas and/or particles. The invention also relates to an unmanned aerial vehicle (UAV) and the collection of wind data by a moving UAV using at least one wind sensor.

BACKGROUND OF THE INVENTION

Emissions impact both climate and air quality significantly, yet many emissions remain sparsely documented due to the lack of cost-efficient and accurate methods for determining their location and contributions to climate change and air pollution. This is particularly true for fugitive or diffuse emissions from e.g., fossil and/or bio energy production, landfills, wastewater treatment, animal production, other surface area emissions, fires, flares, or other similar drifting emission scenarios. Some of these emissions may also be caused naturally, such as the release of methane through soil layers or similar discharges into the atmosphere from natural deposits. Even in the case of certain stack emissions, such as from vessels at sea or in port, or from land-based facilities, the emissions impact can be hard to determine without reliance on in-stack emissions data which may or may not be available.

With an increased global focus on climate change and air pollution, and an urgent need to counter harmful emissions through the effective application of mitigating strategies and reduction technologies, the ability to reliably and cost-effectively measure the quantity and source origin of fugitive and diffuse emissions becomes central to curbing negative climate and environmental impacts. In particular, accurate monitoring of gaseous emissions of methane ($CH_4$), ammonia ($NH_3$), carbon dioxide ($CO_2$), nitrous oxide ($N_2O$), sulphur dioxide ($SO_2$), and nitrogen oxides (NOx), as well as particle emissions, is of growing concern because of their potent nature or increasing occurrence, although other gases with potential climate and environmental impacts are also relevant.

Determining quantity and source origin of emissions involves the reliable measurement of atmospheric concentrations (of gases or particle size and count), wind speed and direction in a substantially vertical surface downwind from a target source, effectively documenting a vertical cross-section ("inspection area") of the drifting emissions plumes to determine the emission rate and directional location of the source (or sources). Other methods and technologies documented in prior art have attempted to do this using various airborne techniques.

U.S. Pat. No. 4,135,092 describes a method involving the use of, among other techniques, manned aircraft to map gas concentrations in a vertical plane of inspection downwind from a source, in combination with independent measurements of speed and direction of (mean) wind at an index point near the plane of inspection, using portable masts or balloons.

EP 2 625 500 B1 describes the use of a UAV equipped with a remote detection optical instrument to fly over an inspection area, sufficiently above the emissions plume, to remotely detect mean vertical concentration values, while mean wind speed and direction is measured using diagnostic meteorological models that process data from meteorological stations placed at strategic points in the field to be monitored.

WO 2019/246280 A1 describes a system and a method by which an UAV is used to measure methane concentrations along a vertical plane of inspection downwind from a source, while one or more weather stations, distal from the UAV, in combination with a standard wind speed model, are used to establish the mean wind speed in the area at various heights (vertical wind profile). The vertical wind profile in combination with the concentrations on the plane of inspection is subsequently used to derive an integrated mass flux through the plane.

WO 2019/246283 A1 describes a method by which an UAV is used to locate emission sources using a combination of gas sensors on an UAV, local meteorological data, and an inverse stochastic dispersion model to determine the probable location (back trajectory) of the source or sources based on wind statistics measured separately during each plume event.

WO 2020/086499 A1 describes a system comprising an UAV equipped with a gas sensor for detecting gases of methane, carbon dioxide, hydrogen sulphide, water, ammonia, sulphur oxides and nitrogen to generate a map of atmospheric greenhouse gas concentrations but without the inclusion of a wind component.

US 2018/127093 A1 describes an Unmanned Aerial System (UAS) for use in the detection, localization, and quantification of gas leaks. A gas sensor is mounted to a UAS such that the sensor is positioned in a region unaffected by prop wash that is relatively undisturbed by the effects of the propeller(s) and other environmental conditions when in use. The location for the gas sensor is selected where the static and dynamic air flow regions are optimal.

US 2020/033157 A1 describes an aircraft, system, and method for sensing and/or releasing chemical agents by an aircraft is disclosed. The aircraft, system, and method may employ a chemical sensor, a wind sensor, an imaging device for capturing environmental features, and/or a processor operably coupled therewith. The aircraft may be used to detect a chemical plume comprising a predetermined chemical agent. The processor may be used for collecting data from the chemical sensor, the wind sensor, and the imaging device to identify a navigational waypoint and to provide commands to the chemical sensor or to the aircraft based at least in part on collected data.

Several of the methods described in prior art have limited application due to the impractical nature of the design, and/or rely heavily on mean-averaging techniques, various modelling methodologies, and/or third-party data to estimate emission rates and origin. In particular, existing methods and systems rely heavily on model and/or mean approaches to estimate wind speed when determining flux in the inspected area, instead of measuring actual wind conditions along the inspected plane. Where the methods attempt to capture relative wind conditions from the UAV, they do not incorporate the ability to adjust the position of the wind sensor(s) to mitigate dynamic wind impacts during flight caused by shifts in the mean true wind speed/direction, and/or shifts in the speed/direction of the aircraft (including stops and turns). Instead, in all prior art such sensors are described or depicted as immobile fixtures, positioned only to account for the downwash effect from the rotors neglecting other wind factors. Additionally, prior art only describes the application of a single wind sensor, with no disclosure of the application of multiple sensors on a single aircraft. Due to these limitations, the solutions do not adequately capture the actual micro conditions in the inspection area, including accurate measurement of the (shifting) relative wind, and/or the precise correlation of gas concentrations and wind components in time and space. This ultimately increases the uncertainty in quantifying and locating the source of the targeted emissions. Recent studies (Ravikumar, Sreedhara, et. al., 2019) demonstrating various techniques for assessing emissions rates and locations, including several of the techniques mentioned above, thus conclude that the reliance on, among others, (inverse) models to quantify emissions leads to significant uncertainties in the estimations, often with estimated emissions rates varying more than 2× from the actual emissions, i.e., either measuring 50% less or 200% more than the control source emission.

SUMMARY OF THE INVENTION

On the above background it is a subject of the invention to provide a cost-efficient and reliable method for determining emissions from one or multiple sources using UAV technology.

In a first aspect, the invention provides a method for determining emissions from at least one source, the method comprising the steps of:

providing an unmanned aerial vehicle (UAV) comprising:
an electronic control system for controlling the vehicle's flight;
a positioning system for determining the position of the UAV;
at least one emissions sensor for determining the presence or concentration of at least one gas and/or particles;
at least one wind sensor for determining measured wind speed and measured wind direction;
at least one positioning structure for positioning the at least one wind sensor relative to a centre of the UAV;
a data interface for collecting data during flight, the data interface being configured to store said data onboard the UAV and/or pass said data to an external data collection unit, said data comprising at least one of: a first output signal from the electronic control system representing the position of the wind sensor, a second output signal from the positioning system representing the position of the UAV, a third output signal from the at least one emissions sensor, a fourth output signal from the at least one wind sensor representing the measured wind speed and measured wind direction;
controlling the UAV to:
fly through an inspection area along a flight trajectory;
position the at least one wind sensor substantially perpendicular to the measured wind direction at an offset position relative to the centre of the UAV;
collect data by use of the data interface during flight, and/or transmitting said data to an external data collecting unit for further processing thereof;
determining said emissions by combining data from the at least one emissions sensor with data from the at least one wind sensor, and with data from the positioning system, the data from the emission sensor, the wind sensor, and the positioning system being collected during movement of the UAV along the flight trajectory.

Thanks to the provision of the UAV and the method which includes collection of data representing gas concentrations and/or particles as well as measured wind, it is possible to quantify and locate said emissions efficiently in 'one independent UAV setup' without reliance on external sources or equipment to determine meteorological conditions on site, in particular wind, or on knowledge about the possible location of the sources of the emission. The data may be continuously collected, either as independent data points or sets of data or both.

As opposed to the existing prior art, the present invention includes the ability to, with greater precision, simultaneously determine presence or concentration of at least one gas and/or particles and measure wind speed and wind direction from onboard the UAV while taking into account, in particular, the dynamic nature of the wind component during flight.

By measuring both presence/concentration and wind speed and wind direction throughout the inspection area, it is possible to correlate the collected data in time and space to thereby create a consistent representation of the flux density across the inspection area, enabling the calculation of the emission rate(s) of the source(s).

By positioning the at least one wind sensor substantially perpendicular to the measured wind direction in an offset position relative to the centre of the UAV, the impact of the UAV-generated air flow and the mean true wind on the wind measurements may be addressed, whereby the critical issue of these impacts may be eliminated or at least considerably reduced. The distance between the offset position to the centre of the UAV may as an example be at least of 1 m, such as at least 1.5 m, such as at least 2 m, such as at least 2.5 m, such as at least 3 m, or even more. The distance may depend on the size of the UAV.

By 'an offset position relative to the centre of the UAV' should be understood that the at least one wind sensor is positioned at a distance from the centre, where the distance is large enough to avoid impacts from the UAV-generated air flow on the wind measurements during flight and large enough to control the angle by which the relative wind impacts the at least one wind sensor, particularly when the UAV alters course or speed, and/or the mean true wind changes speed and/or direction. The at least one wind sensor can be positioned and repositioned during flight to ensure that the at least one wind sensor is still positioned substantially perpendicular to the measured wind direction, e.g., if the mean true wind direction or wind speed changes and/or if the flight direction or the speed of the UAV is changed.

In the context of the present invention the term 'substantially perpendicular to the measured wind direction' should be understood to mean that the at least one wind sensor is positioned at an angle relative to the measured wind direction being within 20 degrees from perpendicular.

The centre of the UAV may be preferably defined as the geometrical centre of the UAV. In an alternative embodiment, the centre may be the gravitational centre.

A particular aspect of the present invention is thus to provide a method by which an UAV, equipped with one or more emissions sensors and one or more specifically positioned wind sensors, can be used to directly map a pattern of flux density values across an inspection area. By combining both gas concentration and/or particle count, and wind data (speed and direction) into a representation of flux density values (mass/time) across the inspection area, which may be divided into a substantially vertical plane (also denoted a data grid), at least downwind from the source(s), it is possible to subsequently integrate these values to calculate total flux rates (mass/area/time) through parts of or all of the inspection area, and to associate these rates with one or more sources by their approximate position on the data grid in combination with the associated wind direction data.

The step of collecting data during flight may in one embodiment be carried out by collecting data sets at a determined frequency, wherein each data set comprises a time mark and at least one of: (a) a first output signal from the electronic control system representing the position of the at least one wind sensor, (b) a second output signal from the positioning system representing the position of the UAV, (c) a third output signal from the at least one emissions sensor, and (d) a fourth output signal from the at least one wind sensor representing measured wind speed and measured wind direction.

The electronic control system for controlling the vehicle's flight and the positioning system for determining the position of the UAV may in one embodiment be integrated in a single device configured to control the vehicle's flight and configured to determine the position of the UAV.

It should be understood that the step of controlling the vehicle's flight may be carried out based on an autonomous flight control, e.g., based on a predetermined flight trajectory. In an alternative embodiment, the step of controlling the vehicle's flight may be manual. In a further alternative, autonomous control and manual control may be combined, e.g., by enabling manual control as a supplement to a substantially autonomous control.

The at least one emissions sensor for determining the presence or concentration of at least one gas and/or particles may be detachably attached to the UAV thereby enabling replacement of the emissions sensor(s), e.g., due to calibration, maintenance, or repair, or replacement to a different type, or types, of emissions sensor(s) depending on the gas(es) and/or particles of interest.

The method may further comprise a step of determining the flight trajectory prior to take off. The determination of the flight trajectory may as an example be based on at least one of; information relating to the position of the at least one source, mean wind direction and/or mean wind speed on site, topography of the site at which the source is located, the expected type of emissions, weather forecasts, etc.

The method may comprise a step of adjusting the determined flight trajectory during flight, e.g., due to change of meteorological conditions, remaining battery capacity of the UAV, obstacles in the terrain, or any other parameter detectable by on-board equipment or remote equipment, or on the basis of manual intervention from a remote, control facility.

The flight trajectory may be formed at least partly in a predetermined, substantially vertical plane corresponding to the inspection area. In another embodiment, the flight trajectory may be adjusted during flight, e.g., by using an altimeter to allow the trajectory to follow the terrain. Emission and wind (speed and direction) may be determined at a plurality of measurement point at the vertical plane to thereby provide a grid of measurements.

In the context of the invention, the term substantially vertical plane should be understood as a plane being within 20 degrees from vertical.

In one embodiment, the substantially vertical plane may be located at a predetermined distance to the at least one source. The predetermined distance may as an example depend on at least one of mean wind direction, mean wind speed, topography of the site at which the source is located, the expected type of emissions, weather forecasts, etc. Thus, it should be understood, that for one type of emissions, the predetermined distance may be larger than for another type of emission, even if other circumstances are unchanged.

The vertical plane may be formed by substantially horizontal lines which may be denoted transects, where each line/transect may traverse the plane at a determined altitude or height above ground. The horizontal transects traversing the plane may in one embodiment be arranged with equidistant distance. Alternatively, the distance between the horizontal transects may vary across the vertical plane, including increasing or decreasing distances, a mix of both, or random distances.

In one embodiment, the substantially vertical plane may comprise a single substantially horizontal transect shaped like a spiral encompassing the at least one source.

The method may comprise a step of determining a mean wind direction prior to take off, and a step of arranging the substantially vertical plane downwind from the at least one source. The vertical plane may be located substantially perpendicular to a mean wind direction.

As it may be beneficial to be able to determine a background level, i.e., a level of gas and/or particles which do not originate from the at least one source, the method may further comprise a step of determining a mean wind direction prior to take off, and a step of arranging a substantially vertical plane in which the flight trajectory is formed upwind from the at least one source. The substantially vertical plane may be located substantially perpendicular to a mean wind direction. The gas and/or particle level(s) determined upwind form the at least one source may substantially constitute a background level.

Thus, the method may be used to map upwind conditions to establish background levels or isolate a source from other sources in the immediate vicinity by subtracting their contribution to the drifting plumes from that of the (target) source(s).

Alternatively, or additionally, data collected from a substantially vertical plane downwind from the at least one source may be used to both determine emissions from the at least one source and determine background level(s) of gas and/or particles through various statistical methods and/or other means.

As the inspection area may take various shapes depending on the local topography and conditions, number of sources etc., the substantially vertical plane into which the inspection area may be divided may likewise take various shapes.

In one embodiment, the substantially vertical plane may be a single flat plane. In another embodiment, the substantially vertical plane may be composed of a plurality of flat planes to thereby form an edged plane, in which two neighbouring planes abut each other at an angle, e.g., at an angle up to 10 degrees, such as at an angle up to 25 degrees, or at an even larger angle.

In one embodiment, the substantially vertical plane may form at least a partly curved inspection area, partially or fully surrounding the at least one source. By a curved inspection area should be understood, a vertical plane which in a horizontal cross-section forms a curve. Thus, the substantially vertical plane may form a cylinder surrounding the at least one source or a section of a cylinder partly surrounding the at least one source. It should be understood, that the substantially vertical plane may be a combination of both a partly curved plane and a flat plane and/or a plurality of flat planes, e.g., by a vertical plane abutting a section of a cylinder.

By controlling the UAV to fly a fully or partly curved flight trajectory along a curved plane, both upwind and downwind emissions can be measured, and adjacent sources may be excluded, effectively enabling emissions from the at least one source to be isolated from any adjacent emission sources that may otherwise contaminate the measurement results. This may thus be an alternative way of determining a background level.

As described above, a data grid may be formed by flying the UAV along the flight trajectory in the substantially vertical plane, while data is collected continuously along the flight trajectory at a determined frequency to ultimately form a pattern of observation points P(i), i.e. a data grid. The frequency may either be determined by a Hz signal, fixed or variable, or by a specific position in time and space of each observation point P(i) on the vertical plane.

The data may comprise at least one of: a first output signal from the electronic control system representing the position of the at least one wind sensor, a second output signal from the positioning system representing the position of the UAV, a third output signal from the at least one emissions sensor, a fourth output signal from the at least one wind sensor representing the measured wind speed and measured wind direction. The first output signal may alternatively represent both the position and the orientation of the at least one wind sensor.

The ability of the UAV by way of its flight trajectory to adapt to local terrain conditions and overcome obstacles otherwise restricting access to an inspection area, may be considered a key advantage of the method. Similarly, the flexibility to deploy the UAV in multiple measurement scenarios, with the ability to adapt the flight trajectory, and by this the positioning and contours of the data grid, and the speed by which mapping can be done, may greatly reduce the costs involved in measuring drifting emissions, and may enable data collection at locations, conditions, and on sources otherwise difficult to measure.

Further to the invention, the ability to correctly measure the apparent wind onboard the UAV during flight, without material disturbance from the flow of air caused by the UAV itself, and to correctly account for shifting relative wind directions impacting the sensors during flight, either due to the movement of the aircraft during measurement or changes in the mean true wind, may also be considered a key advantage of the method.

The apparent wind is defined as the speed and direction of wind indicated by a wind instrument (such as an anemometer) on a moving vehicle in undisturbed air. If the apparent wind speed and direction, and the speed and direction of the moving vehicle is known, then the true wind may be determined by normal wind triangulation enabling the calculation of flux in each observation point P(i) along the flight trajectory. (True wind is defined as the wind relative to a fixed ground-based point.)

However, when a UAV flies, it displaces air around the vehicle to create lift and movement which may impact the at least one wind sensor creating a compromised apparent wind signal/a compromised measured wind speed and wind direction signal. To overcome this issue, the wind sensor may be positioned at an offset position relative to the centre of the UAV to reduce or mitigate any such air displacement caused by the UAV itself, and substantially perpendicular to the measured wind direction to account for changes in the angle of the relative wind hitting the wind sensor, whereby the measured wind speed and measured wind direction may correspond substantially to the apparent wind speed and direction.

The step of positioning the at least one wind sensor at an offset position relative to the centre of the UAV may be based on optimizing the distance between the wind sensor and the centre of the UAV, effectively positioning the at least one wind sensor at an appropriate distance away from the rotors. To achieve such distance, the at least one positioning structure for positioning the at least one wind sensor relative to the centre of the UAV may in one embodiment comprise an elongated structure, e.g., an extended boom arm, attached to the UAV at one end while the at least one wind sensor is attached to an opposite end. In an alternative embodiment, the positioning structure may comprise a substantially disc-shaped structure having an edge portion at an appropriate distance to the rotors at which the at least one wind sensor is attached.

Thus, in one embodiment, the unmanned aerial vehicle may comprise a positioning structure comprising at least one a boom arm, wherein the at least one wind sensor is positioned substantially at one end of the at least one boom arm.

To minimise or even eliminate impact from the UAV on the at least one wind sensor, a size of the positioning structure, such as a length of the at least one boom arm may be larger than a rotor radius of the UAV to allow the at least one wind sensor to be positioned outside the rotor radius of the UAV. The length of the elongated structure, such as the length of the boom arm, may as an example be at least of 1 m, such as at least 1.5 m, such as at least 2 m, such as at least 2.5 m, such as at least 3 m, or even more. The length may depend on the size of the UAV.

The step of positioning the at least one wind sensor may further comprise a step of changing the position of the wind sensor relative to the measured wind direction. In one embodiment, such movement may be achieved by moving the positioning structure independently of the centre of the UAV. In another embodiment, such movement may be achieved by rotating the UAV, including the positioning structure, relative to a yaw axis of the UAV. Thus, the positioning structure may be a fixed structure ensuring a predetermined distance between the at least one wind sensor and the centre of the UAV. Positioning of the at least one wind sensor substantially perpendicular to the measured wind direction may thus be achieved by rotating the UAV including the positioning structure relative to the yaw axis.

Alternatively, the positioning structure may be a movable structure allowing at least one of horizontal, vertical, or rotational movement of the at least one wind sensor relative to the centre of the UAV.

The position of the at least one wind sensor substantially perpendicular to the measured wind direction and offset relative to the centre of the UAV may be adjusted during flight, e.g., as a response to changing the flight direction and/or speed of the UAV and/or when the mean true wind direction and/or speed changes. To adjust the positioning of the at least one wind sensor relative to the measured wind direction during flight, the step of positioning the at least one wind sensor may in one embodiment be continuously repeated during flight. In an alternative embodiment, the position may be changed whenever the flight direction changes.

At least for some wind sensors it may be an advantage, if the wind sensor is substantially horizontally arranged during measurements of wind direction and/or wind speed. During flight, the UAV may be non-horizontally arranged, e.g., as a front part of the UAV may be arranged at another height than a rear part, such as lower. Thus, the UAV may be arranged in the tilted position during flight, also denoted the pitch of the aircraft. Similarly, a left part of the UAV may be arranged at another height than the right part (or oppositely), such as lower, also denoted the roll of the aircraft. The method for determining emissions may therefore comprise a step of determining a tilted position of the UAV (right/left and/or front/rear), where the tilted positioned is defined as a position of the UAV relative to a horizontal plane, and a step of tilting the wind sensor in response to the tilted position.

Consequently, it may be possible to compensate the position of the at least one wind sensor for a non-horizontal position of the UAV. As an example, the at least one wind sensor may be tilted by tilting the positioning structure relative to the centre of the UAV. In an alternative embodiment, the at least wind sensor may be pivotally attached to the positioning structure to enable tiling of the wind sensor.

It should be understood, that positioning of the at least one wind sensor relative to the centre of the UAV and the measured wind direction includes at least one of horizontal movement, vertical movement, or rotational movement. In a further alternative, the distance between the at least one wind sensor and the centre of the UAV may also be changed. This may e.g., be achieved by including a telescopic structure in the positioning structure.

The ability to correctly establish true wind in time and space in individual observation P(i) points across the inspection area is a methodological element in relation to the subsequent calculations of emissions rates. Wind direction and speed on a micro meteorological level can vary significantly over an inspection area, particularly in locations where local landscape features (trees, buildings, terrain etc.) influence wind patterns, or where the area comprises crosswinds and/or upwinds as well. A mean wind model, or similar approximations, cannot take these micro meteorological wind variations into account, leading to significant uncertainties on the measurement results.

It should be understood, that the method is not limited to a specific type of source or specific type of emission. Moreover, the method may be applied to a multitude of different source types and measurement scenarios where the ability to independently determine emissions may further rely on the ability to measure the drifting plumes from such sources. This may be particularly relevant in cases with fugitive emissions such as from industrial or energy facilities, farms, ships, open area surfaces, or soils etc., but may also apply to stack monitoring where the determination of emission outputs from a funnel is not supported by in-stack sensors or other means to determine flow rates, gas, and/or particle concentrations.

In one embodiment, the at least one emissions sensor is based on in situ measurement principles as opposed to remote sensing techniques that use optical means to 'look' at a plume from a distance as the method of determination. By measuring in situ, variations in the emissions flux density rates across the inspection area can be mapped in detail, allowing greater granularity and consequently lower uncertainty of the emission rate determination.

The UAV may be equipped with a single emissions sensor or multiple emissions sensors sampling substantially in parallel to obtain a broader simultaneous picture of the contents of the emissions. Examples of such relevant emissions to measure include, but are not limited to, carbon dioxide ($CO_2$), methane ($CH_4$), nitrous oxide ($N_2O$), ammonia ($NH_3$), noxious emissions ($NO_x$), sulphur dioxide ($SO_2$) and/or particle emissions (PM).

In one embodiment of the invention, the at least one emissions sensor may be attached as one or more standalone payloads to the UAV fuselage, or the sensor(s) may be integrated onboard the UAV itself.

In one embodiment, the positioning system may be part of the electronic control system for controlling the vehicle's flight, or it may form a separate system, either integrated onboard the UAV or as part of a standalone payload.

In one embodiment of the invention, the UAV may be equipped with a single wind sensor on a positioning structure, or it may be equipped with multiple wind sensors on the same or separate positioning structures.

In one embodiment of the invention, the at least one wind sensor is configured to determine measured wind speed and measured wind direction at least in a horizontal direction. In another embodiment, the at least one wind sensor is configured to determine measured wind speed and measured wind direction in a vertical direction. In a third embodiment, the at least one wind sensor is configured to measure wind speed and wind direction in both a horizontal and a vertical direction.

In one embodiment, the positioning system may comprise a global navigation satellite system to determine the UAV's position in 3D.

In one embodiment of the invention, the UAV may be equipped with an altimeter configured to determine a height above ground for the vehicle, and in one embodiment use said determined height over ground to dynamically adjust the flight trajectory during flight to conform the vertical inspection area to the terrain.

The method may be used to determine emissions and/or source location, by combining data from the at least one wind sensor and at least one emissions sensor with time-stamped position data obtained from the positioning system during flight. Together, the outputs from these data sets along the flight trajectory may make up a data grid of observation points P(i) along the inspection area. To determine emissions, in particular emissions rates (mass flux) through all or parts of the inspection area, various methods may be applied which may include, but are not limited to, determining the mass flux by calculating the integration of measured emissions concentrations and/or particle count C(i) times wind vectors w(i) across the surface, or a section of the surface, as follows:

$$\text{Mass Flux} = \Sigma_i \kappa \cdot C(i) \cdot w(i) \cdot n \cdot A(i) \text{ [total mass per time unit]}$$

Where:

C(i) is the measured concentration at observation point P(i), corrected for background;

$\kappa$ indicates the conversion factor from volume concentration to mass concentration;

A(i) is the area element at observation point P(i);

w(i) is the true wind observed at P(i) obtained by converting the measured apparent wind to true wind using wind triangulation;

w(i)·n is the component of the true wind w(i) normal (n) to the area element A(i).

The summation above is valid also if the substantially vertical plane into which the inspection area may be divided is curved and/or comprises a plurality of flat planes, i.e. the summation does not assume the area elements A(i) to be neither vertical nor orientated (normal) relative to the mean wind. The area elements A(i) are chosen such that each element is included only once, and such that $\Sigma A(i)$ sums up the total inspection area (or a dedicated section hereof).

In a second aspect, the invention provides an unmanned aerial vehicle (UAV) for determining emissions from at least one source, the UAV comprising:

an electronic control system for controlling the vehicle's flight;

a positioning system for determining the position of the UAV;

at least one emissions sensor for determining the presence or concentration of at least one gas and/or particles;

at least one wind sensor for determining measured wind speed and measured wind direction;

at least one positioning structure for positioning the at least one wind sensor relative to a centre of the UAV;

a data interface for collecting data during flight, the data interface being configured to store said data onboard the UAV and/or pass said data to an external data collection unit, said data comprising at least one of: a first output signal from the electronic control system representing the position of the wind sensor, a second output signal from the positioning system representing the position of the UAV, a third output signal from the at least one emissions sensor, a fourth output signal from the at least one wind sensor representing the measured wind speed and measured wind direction;

the UAV being controllable to:

fly through an inspection area along a flight trajectory;

position the at least one wind sensor substantially perpendicular to the measured wind direction at an offset position relative to the centre of the UAV;

collect data by use of the data interface during flight, and/or transmitting said data to an external data collecting unit for further processing thereof;

wherein said UAV is configured to determine said emissions by combining data from the at least one emissions sensor with data from the at least one wind sensor, and with data from the positioning system, the data from the emission sensor, the wind sensor, and the positioning system being collected along the flight trajectory.

It should be understood, that a skilled person would readily recognise that any feature described in combination with the first aspect of the invention could also be combined with the second aspect of the invention, and vice versa.

The UAV according to the second aspect of the invention is very suitable for performing the method steps according to the first aspect of the invention. The remarks set forth above in relation to the method are therefore equally applicable in relation to the UAV.

BRIEF DESCRIPTION OF THE DRAWINGS

Embodiments of the invention will now be further described with reference to the drawings, in which.

DETAILED DESCRIPTION OF THE DRAWINGS

It should be understood that the detailed description and specific examples, while indicating embodiments of the invention, are given by way of illustration only, since various changes and modifications within the spirit and scope of the invention will become apparent to those skilled in the art from this detailed description.

Figure 1:
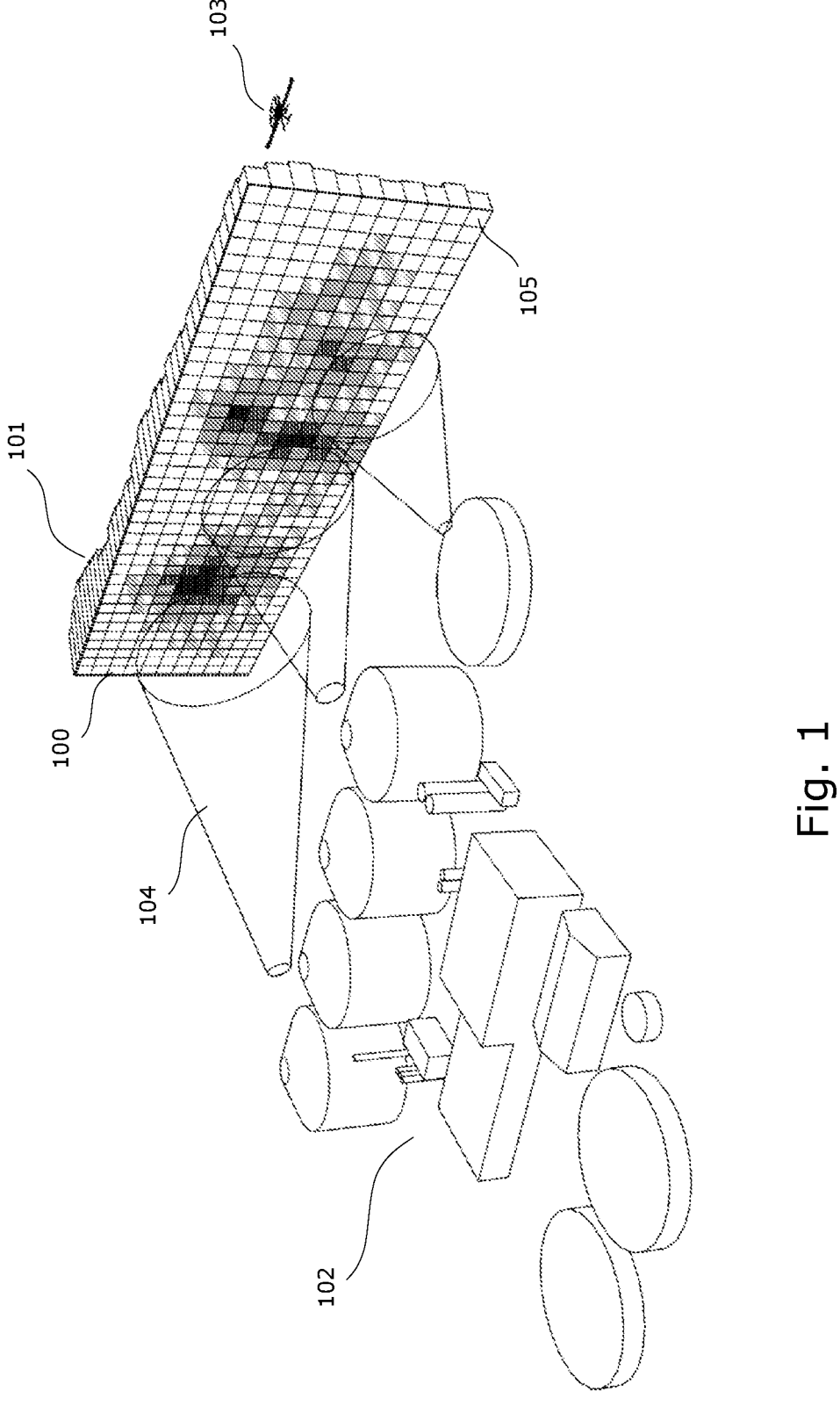
FIG. 1 illustrates an inspection area divided into a substantially vertical plane 100 and an associated data grid 101, placed downwind from at least one source 102 and mapped by a UAV 103, as derived using the method.

FIG. 1 generally shows an inspection area divided into a substantially vertical plane 100 (marked with dotted lines) placed downwind from a source 102 with each cone representing a least one plume of drifting emissions 104 from the source 102. The vertical plane 100, when flown by the UAV 103 in one embodiment of the invention, forms a data grid 101 of observation points and associated area elements, each element illustrated by a coloured grid block representing emissions flux 105 in the data grid 101. The colour and depth of each grid block 105 illustrating respectively varying concentration values and/or particle counts, and wind vectors determined across the inspection area using the method. Combined, the concentrations and wind vectors may be used to calculate a mass flux value in each observation point and further integrated to calculate a total mass flux rate through parts or all of the vertical plane 100. As illustrated, in one embodiment of the invention a source 102 may in fact consist of several sub-sources each emitting an emission plume 104, leading to a subdivision of the data grid 101 in sections representing different sub-sources. The UAV 103 may fly though the inspection area along a flight trajectory which is formed in a substantially vertical plane 100 to thereby provide the grid 101.

Figure 2:
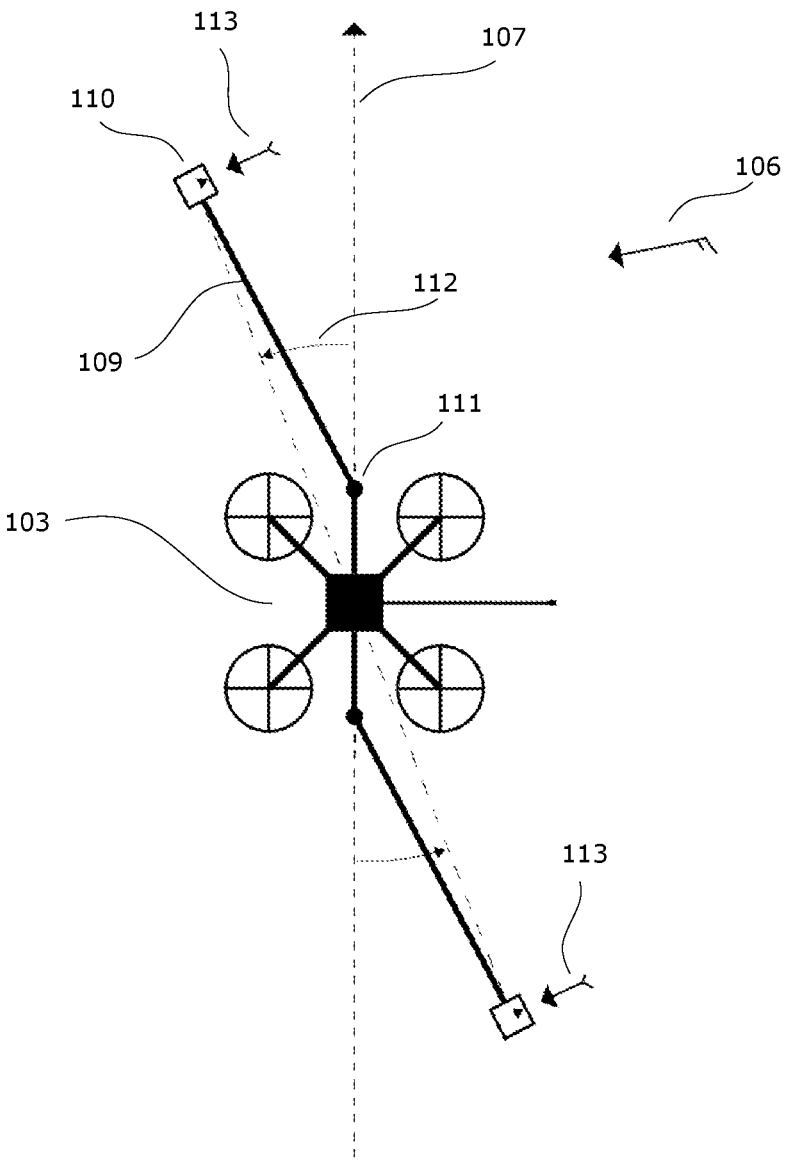
FIG. 2 illustrates a first embodiment of a positioning structure 109 on the UAV 103 and the positioning of the at least one wind sensor 110 during flight.

FIG. 2 illustrates a first embodiment of a positioning structure 109 on the UAV 103 in which the positioning of the at least one wind sensor 110 relative to the measured wind direction 113 and offset from the centre of the UAV 103 is controlled via an adjustable joint 111. As the UAV 103 moves along the flight trajectory 107, the wind sensor 110 is dynamically (re)positioned based on the measured wind direction 113 during flight by way of moving the positioning structure 109 at an angle 112 (up to ±90 degrees) relative to the centre of the UAV 103. If/when the measured wind direction 113 changes during flight, for instance because of changes in the mean true wind direction 106 or speed, the angle 112 is adjusted to once again reposition the wind sensor 110 at an optimal position during flight; i.e. at a position substantially perpendicular to the measured wind direction. The positioning structure 109 may also be rotated and/or tilted along its own axis to compensate for the forward pitch and/or roll of the aircraft during flight.

Figure 3:
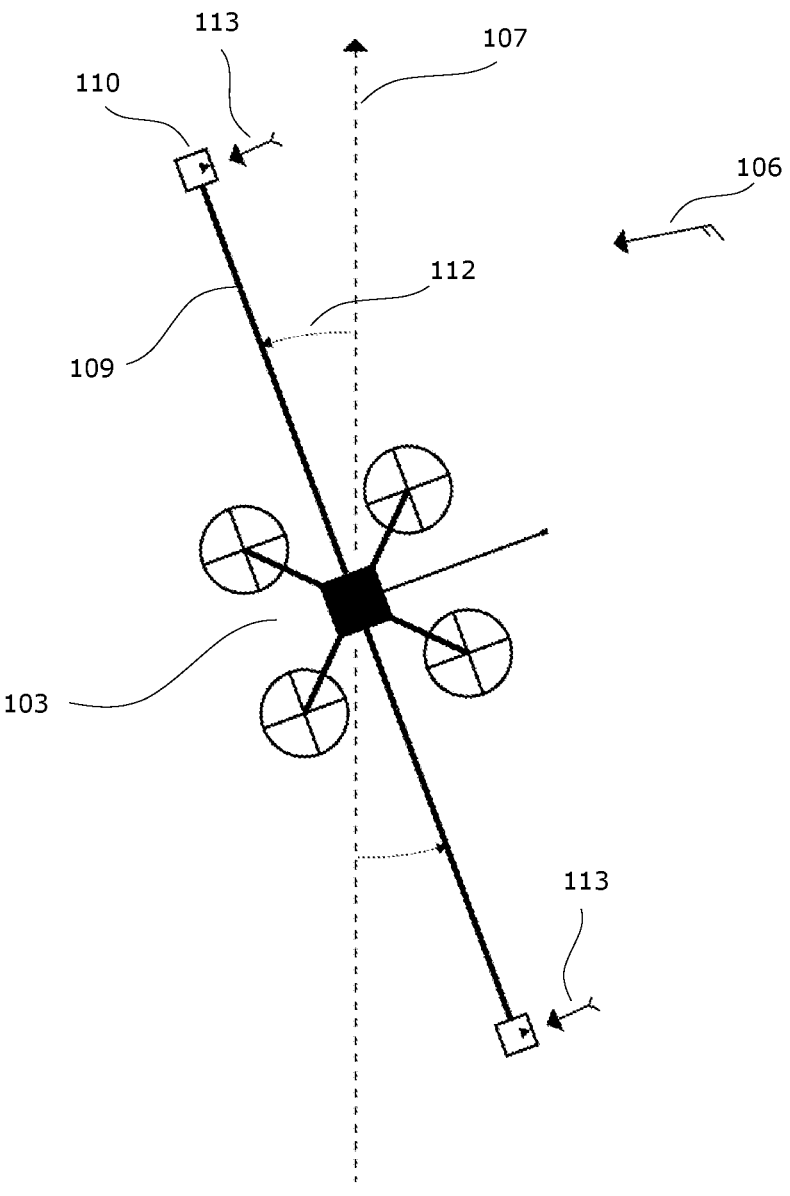
FIG. 3 illustrates a second embodiment of a positioning structure 109 on the UAV 103 and the positioning of the at least one wind sensor 110 during flight.

FIG. 3 illustrates a second embodiment of a positioning structure 109 on the UAV 103 in which the (re)positioning of the at least one wind sensor 110 relative to the measured wind direction 113 is achieved by rotating the UAV 103 along the yaw axis of the UAV 103 itself, including the positioning structure 109, to the optimal angle 112 based on the measured wind direction 113 to thereby position the at least one wind sensor 110 at a position substantially perpendicular to the measured wind direction 113.

Figure 4:
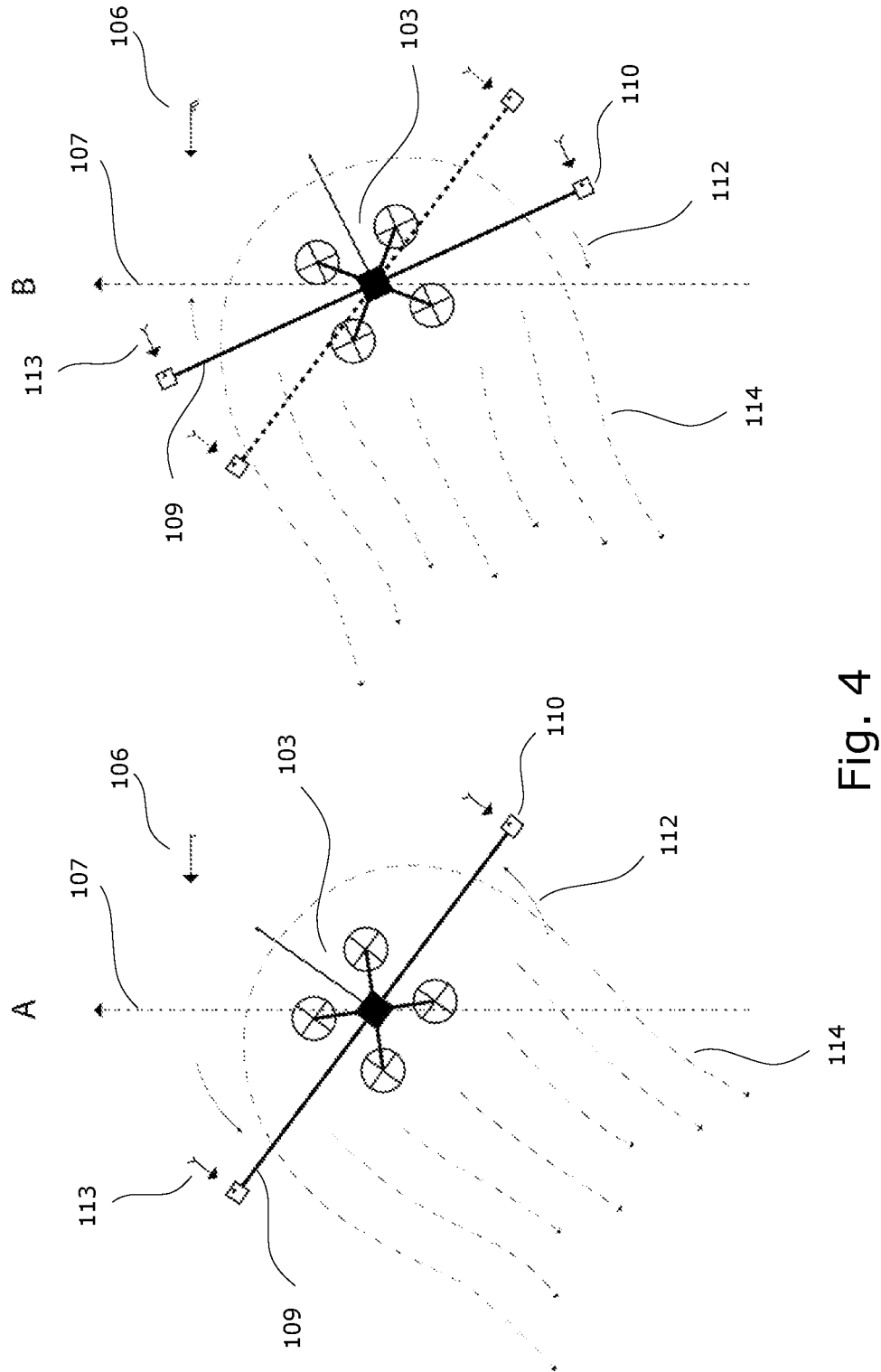
FIG. 4 illustrates differences in the measured wind direction 113 during flight and their subsequent impacts on the (re)positioning of the positioning structure 109 and the least one wind sensor 110.

FIG. 4. illustrates a top view of how the at least one wind sensor 110 is (re)positioned by adjusting the angle 112 of the positioning structure 109 relative to the centre of the UAV 103 based on changes in the measured wind direction 113 and the airflow 114 around the UAV 103. Between scenario A and B, an increase in the mean true wind speed 106 has caused a shift in the measured wind direction 113 and the airflow 114 around the UAV 103, prompting a (re)positioning of the at least one wind sensor 110 by a decrease in the angle 112 of the positioning structure 109 relative to the centre of the UAV 103 to thereby (re)position the at least one wind sensor 110 at a position substantially perpendicular to the measured wind direction. Similar adjustments may also be caused by an increase in the speed of the UAV 103 or a combination of shifts in both UAV 103 speed and/or direction and mean true wind speed and/or direction 106.

Figure 5:
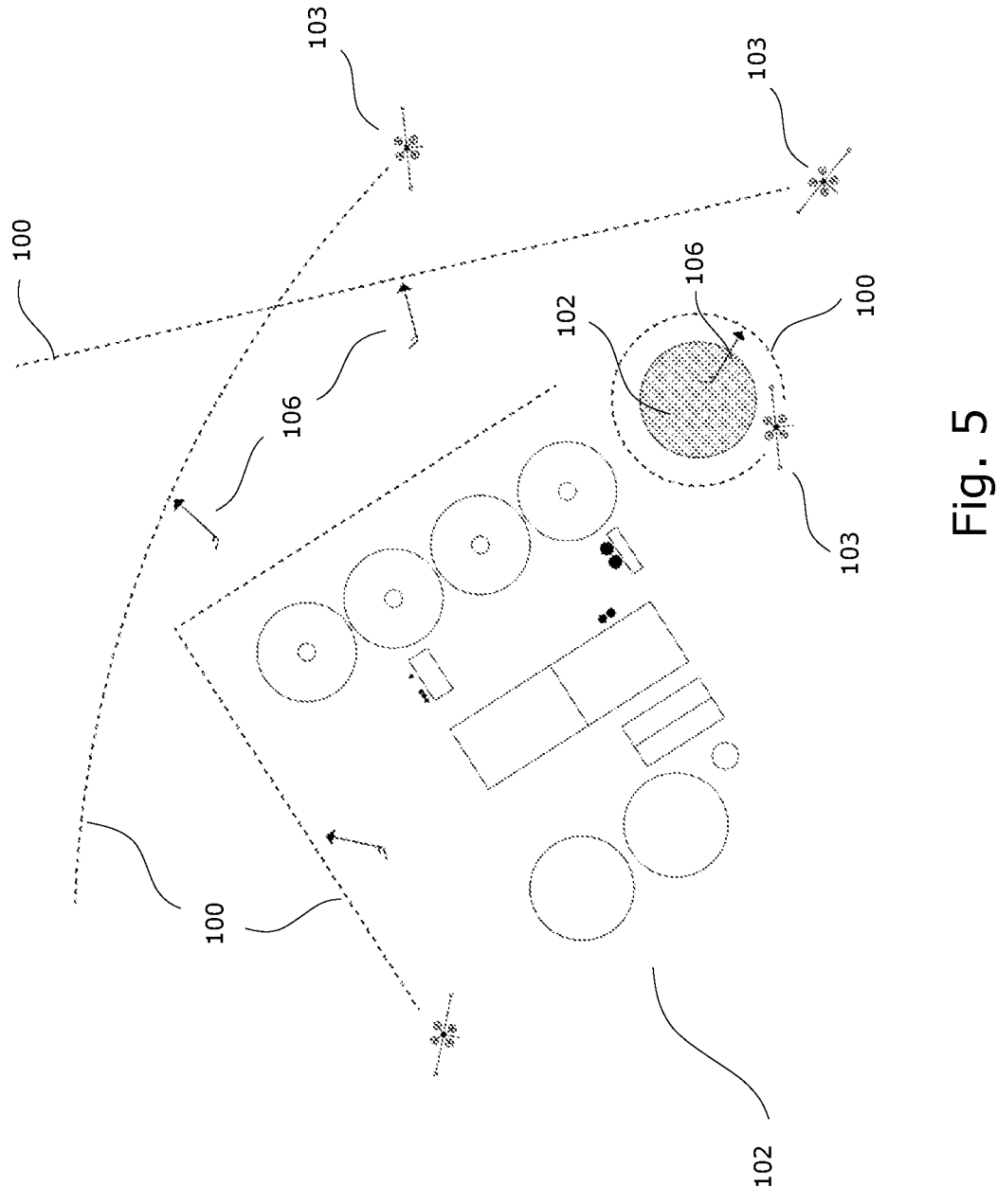
FIG. 5 illustrates a top view of various positions of a vertical plane 100 relative to a source 102 and a mean true wind direction 106.

FIG. 5 illustrates a top view of how an inspection area divided into a substantially vertical plane 100 may be positioned and shaped differently relative to a source 102 and a mean true wind direction 106, each position and shape representing a different application of the method. In one embodiment of the invention the inspection area is shaped as a substantially vertical plane 100 and placed substantially perpendicular to the mean true wind direction 106 at a distance downwind from the source 102. In another embodiment the inspection area 100 is curved (substantially forming a section of a cylinder or a cone) and angled vis-à-vis the mean true wind direction 106. In a third embodiment, the vertical plane 100 encircles a source 102 (the round basin) for the purpose of documenting both upwind and downwind conditions surrounding the source 102 in the same flight. This scenario is particularly relevant in conditions where the emissions from an adjacent source may influence, or contaminate, the measurements on the source 102. The actual shape and positioning of the substantially vertical plane 100 will depend on the conditions on site at the time of measurement.

Figure 6:
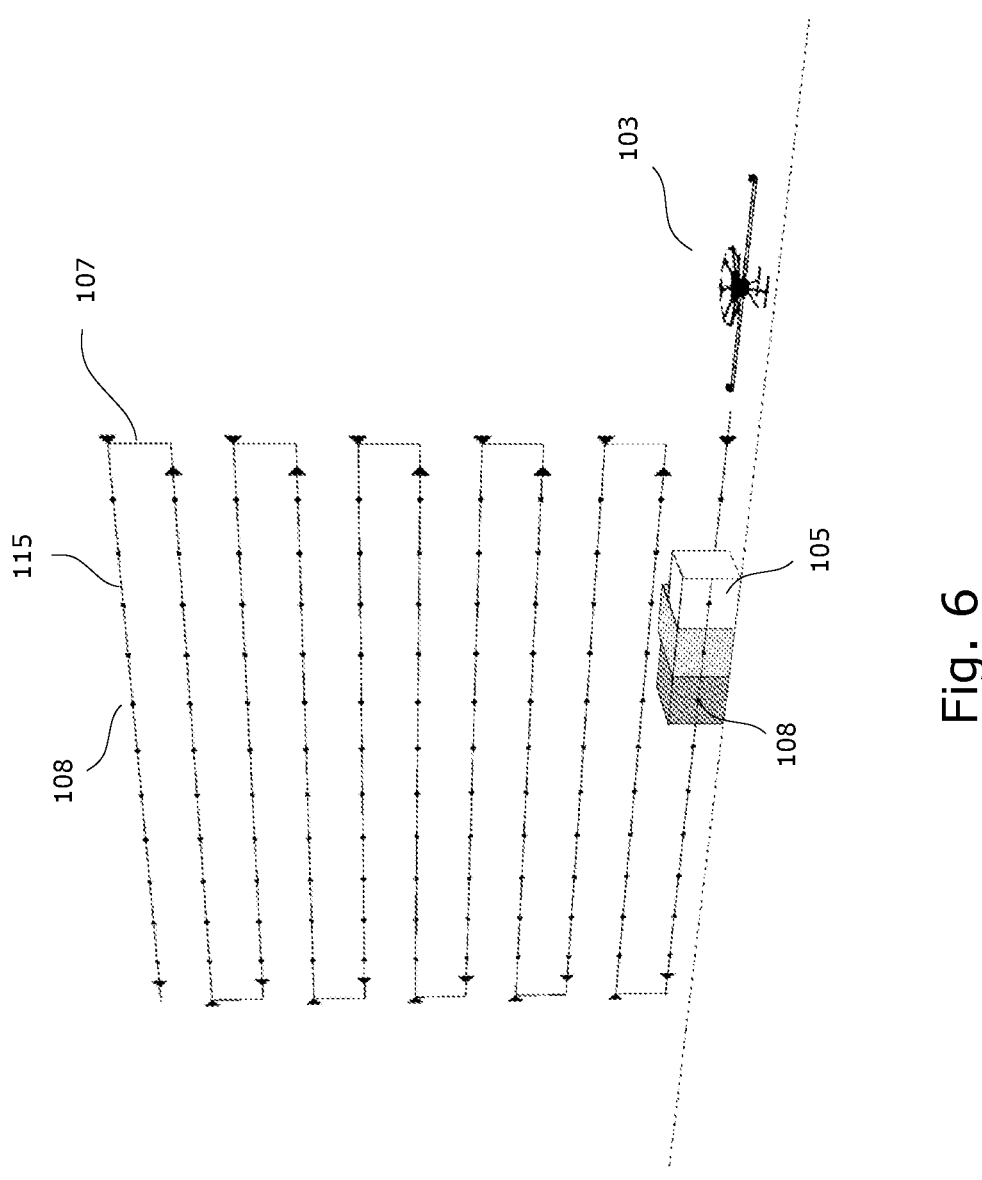
FIG. 6 illustrates a flight trajectory 107 as flown by a UAV 103 with each observation point 108 represented by a dot on the trajectory 107 with an associated area element 105 represented by a coloured grid block.
Figure 10:
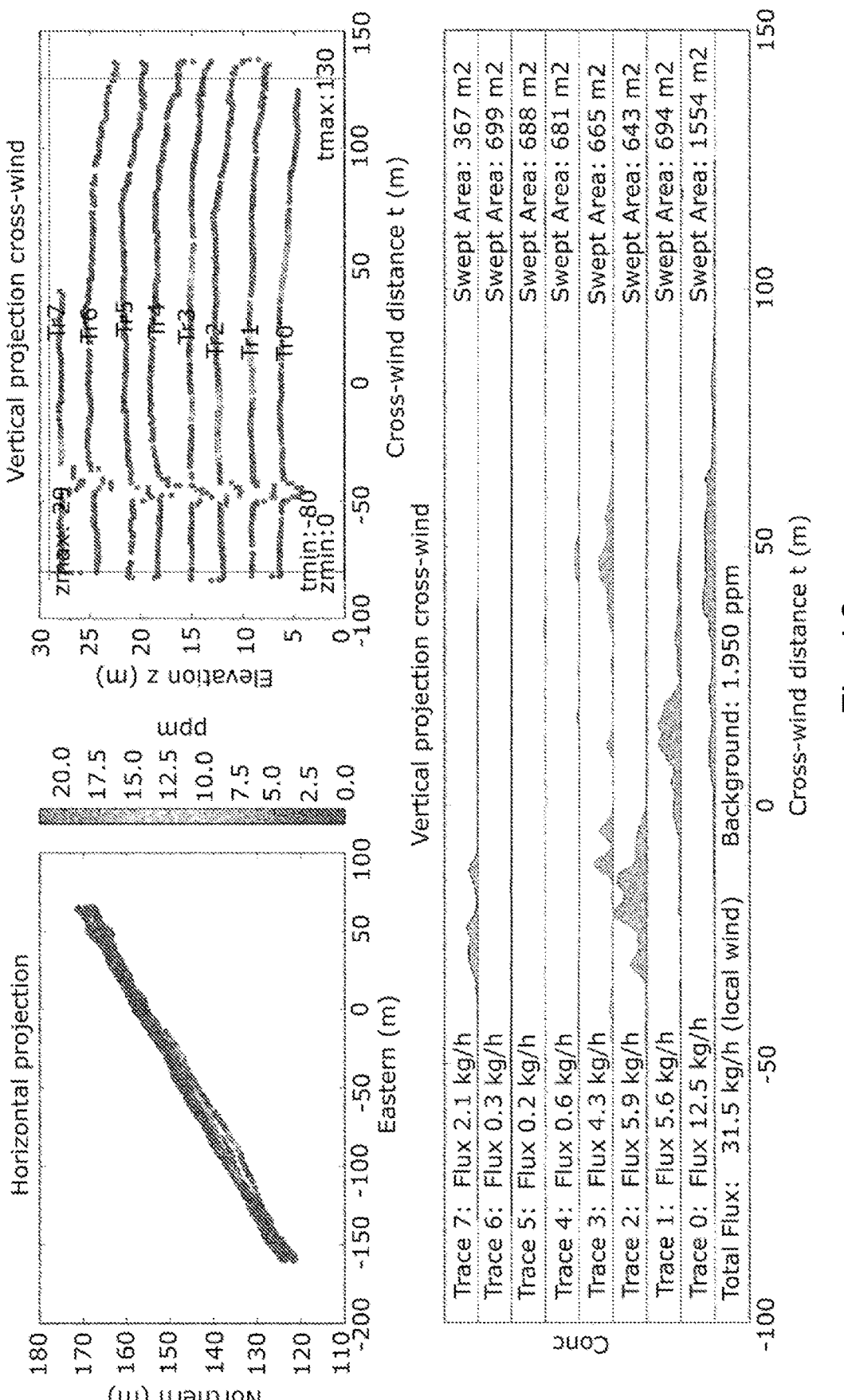
FIG. 10 illustrates a horizontal and vertical projection of a flight trajectory 107 with the recorded observation points plotted as well as an example of a calculated mass flux according to one embodiment.

FIG. 6 illustrates a flight trajectory 107 as flown by a UAV 103 in one embodiment of the invention with each observation point 108 represented by a dot on the flight trajectory 107 and the associated area element illustrated by a coloured grid block representing emissions flux. As the UAV moves along horizontally transects 115 traversing the plane, data is collected continuously along the way at various observation points 108 at a determined frequency. Note, the illustration is highly idealised. Both the exact distance between the observation points and the traversing transects 115, and thus the shape and positioning of the individual area elements 105 will typically vary, creating a more random pattern as illustrated in FIG. 10.

Figure 7:
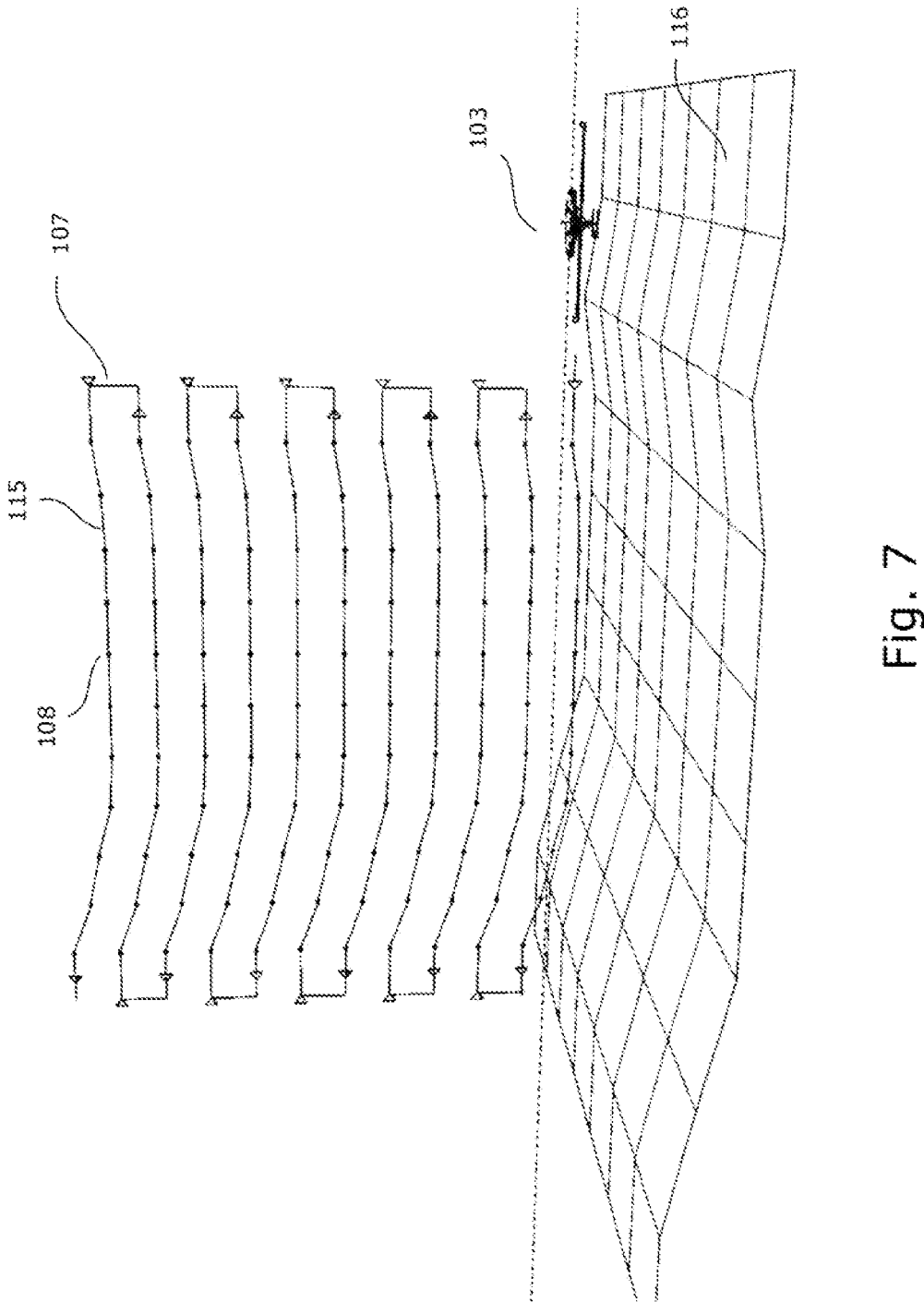
FIG. 7 illustrates a first embodiment of the invention in which the flight trajectory 107 conforms to the terrain 116.

FIG. 7. illustrates an embodiment of the invention in which the flight trajectory 107 conforms to the terrain 116. In this embodiment, the positioning system onboard the UAV 103 may comprise an altimeter to determine height over ground to allow the UAV 103 to adjust the flight trajectory 107 during flight to maintain a substantially fixed distance above terrain.

Figure 8:
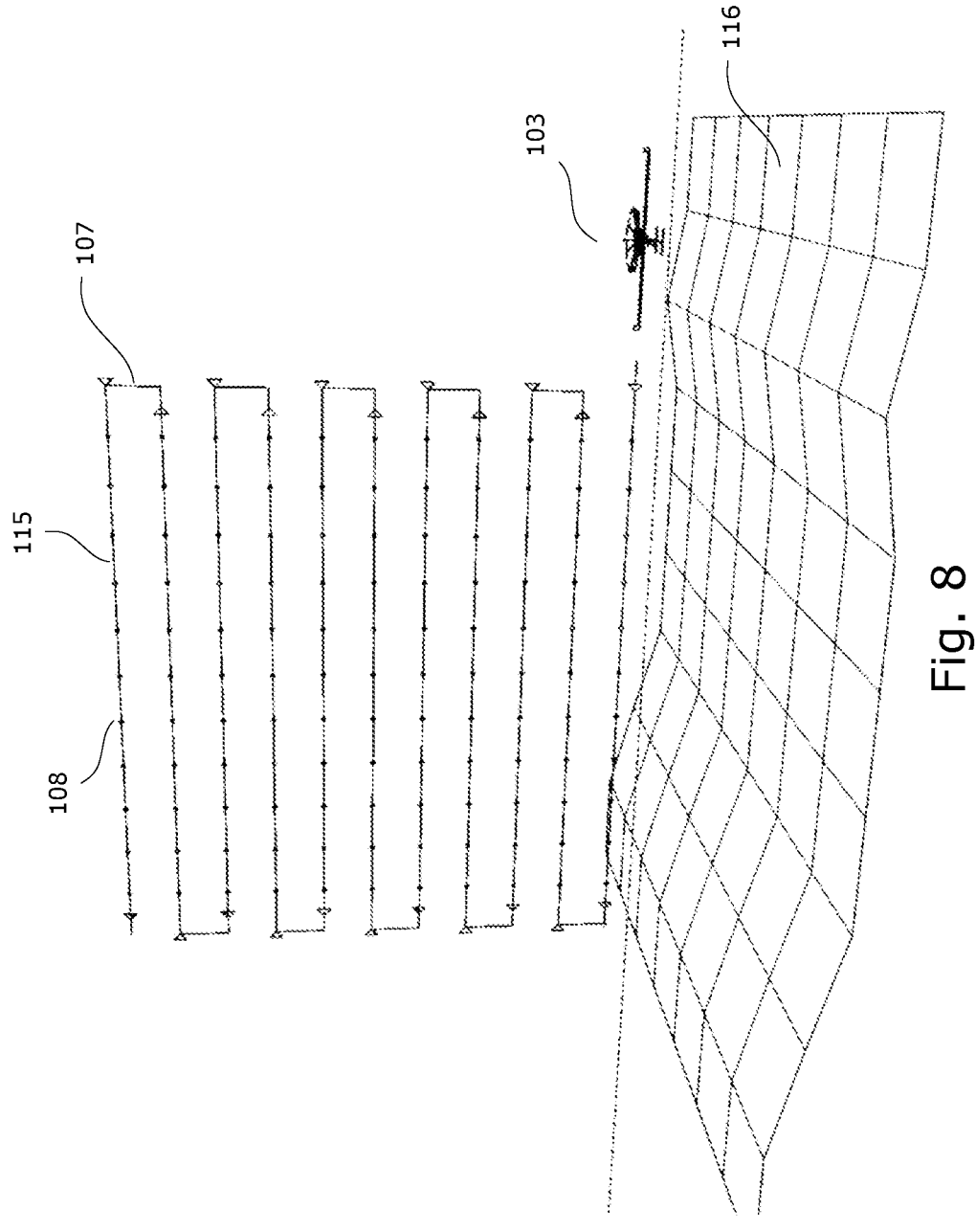
FIG. 8 illustrates a second embodiment of the invention in which the flight trajectory does not conform to the terrain 116.

FIG. 8. illustrates an alternative embodiment of the invention in which the flight trajectory 107 does not conform to the terrain 116. In this embodiment, the flight trajectory 107 is conducted independent of actual elevation above ground. This may be particularly relevant in scenarios where the terrain is substantially flat, the source is elevated, or where measurements are carried out above water.

Figure 9:
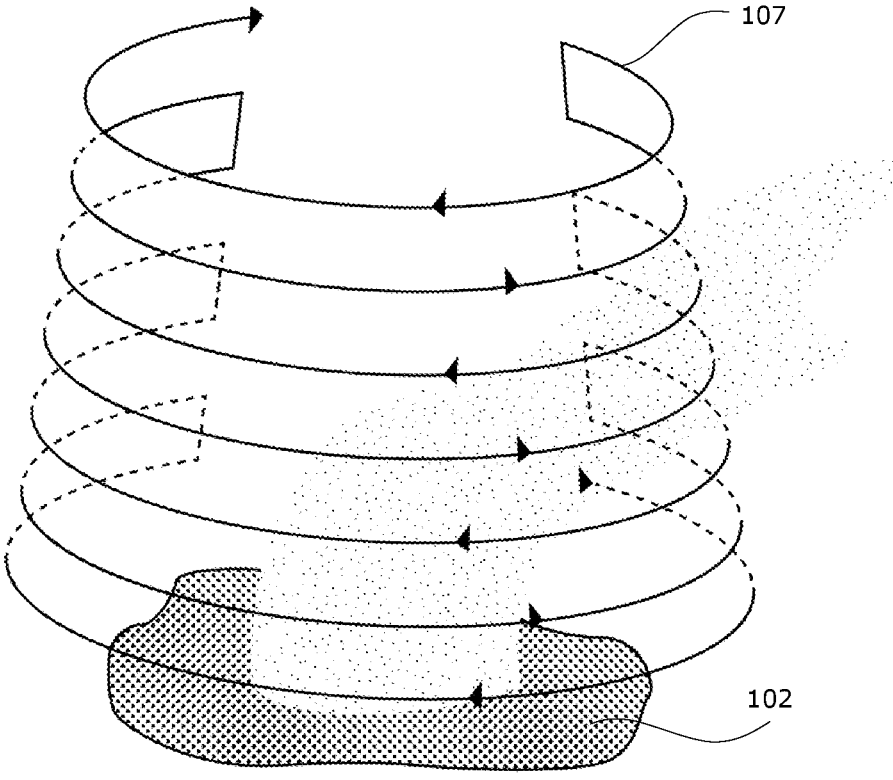
FIG. 9 illustrates a third embodiment of the invention in which the flight trajectory 107 is curved around at least one source 102.

FIG. 9. illustrates a third embodiment of the invention in which the flight trajectory 107 is curved around a source 102. This may be particularly relevant in scenarios where the source 102 is located adjacent to other emission sources that may influence the measurements. By flying a fully or partly circular flight trajectory 107, both upwind and downwind emissions can be measured, effectively enabling emissions from the source 102 to be isolated from any adjacent emission sources that may otherwise contaminate the results. In one embodiment of the invention, the flight trajectory 107 may also be executed as a spiral surrounding the source 107 without alternations of orientation of the flight direction.

FIG. 10 illustrates a horizontal and vertical projection of an actual flight trajectory (top two diagrams) with each dot representing an observation point. In addition, an example of calculation of the corresponding integrated mass flux across the full inspection area is illustrated in the diagram below.

Figure 11:
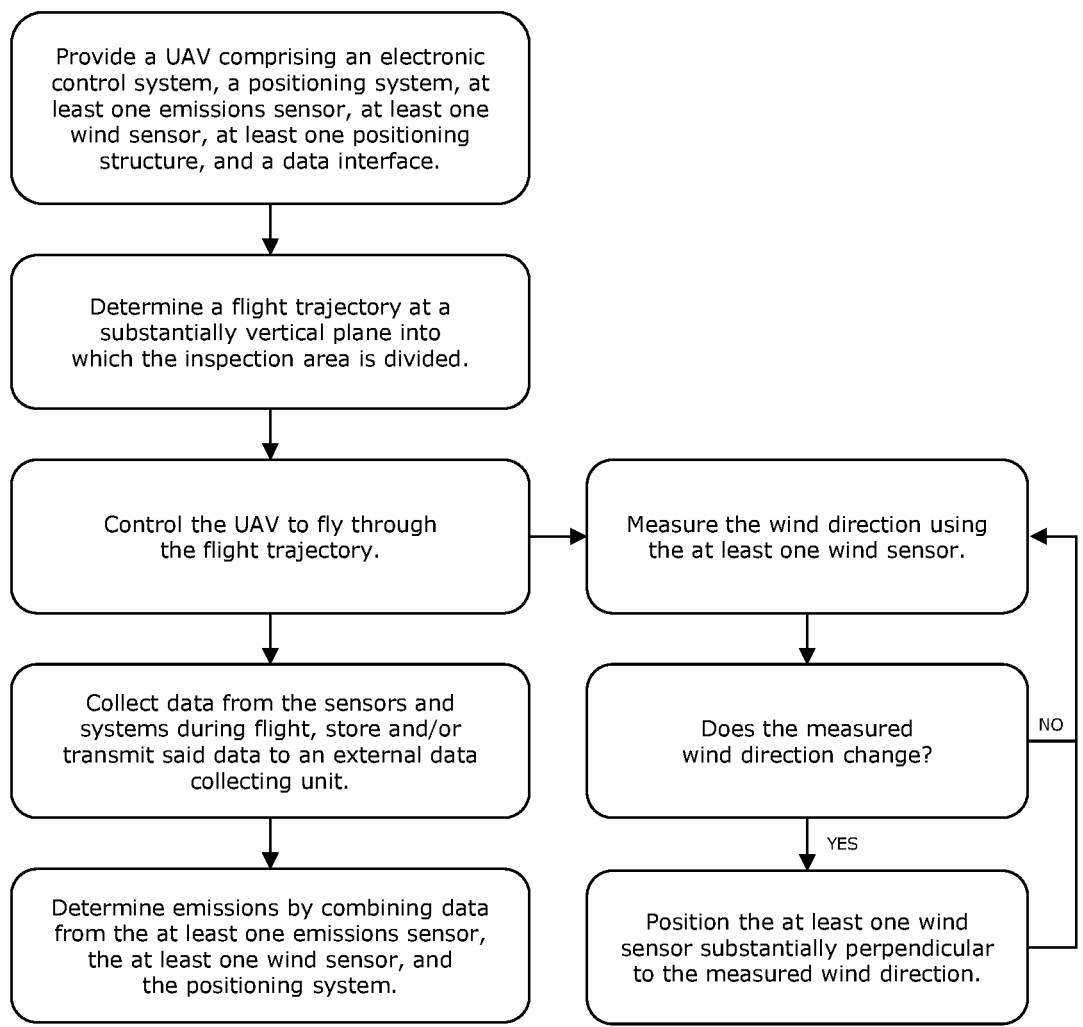
FIG. 11 is a flow chart generally illustrating the steps of one embodiment of the method according to the first aspect of the invention.

FIG. 11 is a flow chart generally illustrating the steps of one embodiment of the method according to the first aspect of the invention, including in particular the steps associated with the dynamic (re)positioning of the positioning structure during flight in response to the measured wind direction.

The invention claimed is:

1. A method for determining emission rates from at least one source, the method comprising the steps of:
  providing an unmanned aerial vehicle (UAV) comprising:
  an electronic control system for controlling the vehicle's flight;
  a positioning system for determining the position of the UAV;
  at least one emissions sensor for determining the presence or concentration of at least one gas and/or particles;
  at least one wind sensor for determining measured wind speed and measured wind direction;
  at least one positioning structure for positioning the at least one wind sensor relative to a centre of the UAV;
  a data interface for collecting data during flight, the data interface being configured to store said data onboard the UAV and/or pass said data to an external data collection unit, said data comprising at least one of: a first output signal from the electronic control system representing the position of the wind sensor, a second output signal from the positioning system representing the position of the UAV, a third output signal from the at least one emissions sensor, a fourth output signal from the at least one wind sensor representing the measured wind speed and measured wind direction;
  controlling the UAV to:
  fly through an inspection area along a flight trajectory;
  position the at least one wind sensor substantially perpendicular to the measured wind direction at an offset position relative to the centre of the UAV,
  wherein positioning of the at least one wind sensor comprises a step of moving the at least one positioning structure relative to the centre of the UAV; and
  wherein the at least one wind sensor is repositioned during flight, if the speed of the UAV is changed,
  collect data by use of the data interface during flight, and/or transmitting said data to an external data collecting unit for further processing thereof;
  determining said emissions by combining data from the at least one emissions sensor with data from the at least one wind sensor, and with data from the positioning system, the data from the at least one emission sensor, the at least one wind sensor, and the positioning system being collected during movement of the UAV along the flight trajectory, wherein the data from the at least one wind sensor and the speed and direction of the moving UAV is used in wind triangulation for calculating a true wind speed, and wherein the true wind speed is used for calculating emission rates.

2. The method according to claim 1, wherein the data are continuously collected.

3. The method according to claim 1, wherein the step of positioning the at least one wind sensor comprises a step of rotating the UAV including the positioning structure relative to a yaw axis of the UAV.

4. The method according to claim 1, further comprising a step of determining a tilted position of the UAV, where the tilted positioned is defined as a position of the UAV relative to a horizontal plane, and a step of tilting the wind sensor in response to the tilted position.

5. The method according to claim 1, wherein the step of positioning the at least one wind sensor is continuously repeated during flight.

6. The method according to claim 1, further comprising a step of determining the flight trajectory prior to take off.

7. The method according to claim 1, wherein the flight trajectory is formed at least partly in a predetermined, substantially vertical plane.

8. The method according to claim 7, wherein the predetermined, substantially vertical plane is located at a predetermined distance to the at least one source.

9. The method according to claim 7, wherein the predetermined, substantially vertical plane is formed by substantially horizontal transects, where each transect is traversing the vertical plane at a determined altitude or height above ground.

10. The method according to claim 7, wherein the predetermined, substantially vertical plane at least partly forms a curved inspection area, partially or fully surrounding the at least one source.

11. The method according to claim 7, further comprising a step of determining a mean wind direction prior to take off, and a step of arranging the substantially vertical plane downwind from the at least one source.

12. The method according to claim 7, further comprising a step of determining a mean wind direction prior to take off, and at step of arranging the substantially vertical plane upwind from the at least one source to determine a background level of gas and/or particles which do not originate from the at least one source, and/or to isolate said emissions from said at least one source from emissions from other sources.

13. The method according to claim 7, wherein the step of collecting data during flight is carried out by sampling data sets at a determined frequency, wherein each data set comprises a time mark and at least one of:

(a) a first output signal from the electronic control system representing the position of the wind sensor, (b) a second output signal from the positioning system representing the position of the UAV, (c) a third output signal from the at least one emissions sensor, and (d) a fourth output signal from the at least one wind sensor representing measured wind speed and measured wind direction.

14. An unmanned aerial vehicle (UAV) for determining emission rates from at least one source, the UAV comprising:

an electronic control system for controlling the vehicle's flight;

a positioning system for determining the position of the UAV;

at least one emissions sensor for determining the presence or concentration of at least one gas and/or particles;

at least one wind sensor for determining measured wind speed and measured wind direction;

at least one positioning structure for positioning the at least one wind sensor relative to a centre of the UAV;

a data interface for collecting data during flight, the data interface being configured to store said data onboard the UAV and/or pass said data to an external data collection unit, said data comprising at least one of: a first output signal from the electronic control system representing the position of the wind sensor, a second output signal from the positioning system representing the position of the UAV, a third output signal from the at least one emissions sensor, a fourth output signal from the at least one wind sensor representing the measured wind speed and measured wind direction;

the UAV being controllable to:

fly through an inspection area along a flight trajectory;

position the at least one wind sensor substantially perpendicular to the measured wind direction at an offset position relative to the centre of the UAV, wherein positioning of the at least one wind sensor comprises a step of moving the at least one positioning structure relative to the centre of the UAV; and wherein the at least one wind sensor is repositioned during flight, if the speed of the UAV is changed, collect data by use of the data interface during flight, and/or transmitting said data to an external data collecting unit for further processing thereof;

wherein said UAV is configured to determine said emissions by combining data from the at least one emissions sensor with data from the at least one wind sensor, and with data from the positioning system, the data from the at least one emission sensor, the at least one wind sensor, and the positioning system being collected during movement of the UAV along the flight trajectory, wherein the data from the at least one wind sensor and the speed and direction of the moving UAV is used in wind triangulation for calculating a true wind speed, and wherein the true wind speed is used for calculating emission rates.

\* \* \* \* \*